United States Patent [19]

Powell et al.

[11] Patent Number: 5,105,026
[45] Date of Patent: Apr. 14, 1992

[54] PROCESS FOR PREPARING A BISPHENOL

[75] Inventors: Joseph B. Powell; Christopher W. Uzelmeier, both of Houston, Tex.

[73] Assignee: Shell Oil Company, Houston, Tex.

[21] Appl. No.: 613,433

[22] Filed: Nov. 15, 1990

[51] Int. Cl.⁵ .................. C07C 37/20; C07C 39/16
[52] U.S. Cl. ............................ 568/727; 568/722; 568/723; 568/724; 568/728
[58] Field of Search ............ 568/722, 723, 724, 727, 568/728

[56] References Cited

U.S. PATENT DOCUMENTS

| | | | |
|---|---|---|---|
| 4,169,211 | 9/1979 | Ligorati et al. | 568/724 |
| 4,469,561 | 9/1984 | Sikdar et al. | 203/39 |
| 4,766,254 | 8/1988 | Faler et al. | 568/724 |
| 4,822,923 | 4/1989 | Li | 568/727 |
| 4,825,010 | 4/1989 | Li | 568/727 |
| 5,001,281 | 5/1991 | Li | 568/727 |

FOREIGN PATENT DOCUMENTS 58-21633  2/1983  Japan ..................... 568/727

Primary Examiner—Werren B. Lone

[57] ABSTRACT

The present disclosure is directed to improving purity of a bisphenol product in a bisphenol by-product isomerization process wherein isomers of bisphenol are isomerized to the desired bisphenol product. During the isomerization, acidic resin fines elute from the acidic ion exchange resin catalyst into the reaction effluent. These resin fines can be filtered effectively and without contamination by a bed of solid particles such as alumina or carbon. The removal of resin fines improves the product quality and yield by eliminating resin particulates and reducing acid catalyzed cracking of bisphenols during purification and finishing steps.

26 Claims, 1 Drawing Sheet

PROCESS FOR PREPARING A BISPHENOL

BACKGROUND OF THE INVENTION

This invention relates to the preparation of a bisphenol. In one aspect, the invention relates to improving purity and yield in a process to manufacture a bisphenol employing an acidic ion exchange resin as an isomerization catalyst.

Bisphenols are used as the starting material in the manufacture of resins such as polycarbonate resins and epoxy resins. It is important that the bisphenol starting material be as pure as possible in order to avoid adverse effects on the properties of the resulting resins.

Bisphenols can be manufactured over a strong acid catalyst such as HCl or an acidic ion exchange resin catalyst by the condensation reaction of a phenol with a ketone or an aldehyde. During the preparation process, bisphenol by-products are formed, reducing the yield of the desired bisphenol. It is known that these by-products such as the o, p'- and o,o'-bisphenol isomers, can be isomerized, and related by products such as trisphenols reverted to the desired p,p'- bisphenol product by contacting a mixed product stream with an acidic ion exchange resin isomerization catalyst, thus increasing the yield of the desired bisphenol.

In certain bisphenol preparation processes, the mixed product stream containing the bisphenol in solution is passed to a crystallization zone in which the bisphenol is recovered from the solution as a solid and a portion of the remaining liquid, or "mother liquor," is passed to a second crystallization zone for further removal of bisphenol and subsequent passage through an ion exchange resin isomerization catalyst for conversion of by-products to the desired bisphenol. The isomerization product stream, minus a small purge to prevent build-up of unconvertible by-products in the recycle system, is then recycled to the second crystallization zone.

However, it has been found that acidic resin fines and strong acids leach from the isomerization catalyst into the isomerization reaction effluent. These resin fines and soluble acidity catalyze cracking of the bisphenol during subsequent purification and finishing steps resulting in lower product purity and a decrease in product yield.

In order to obtain bisphenols with higher purity, it is known to use an amine-based organic anion exchange resin to remove acidic impurities from the mother liquor. Such amine-based resins are expensive and inherently less stable than the catalyst resin, and will not be suitable for use as a catalyst resin fines filter. Use of an amine-based resin can also result in the presence of soluble amines or the reaction products of these amines with phenol in the product stream, which will decrease product quality. When the amine-based resin is used in a recycled system, the soluble amines will in turn poison the acidic ion exchange catalyst upon recycle of unconverted reactant. Such amine-based organic resins are typically regenerated by aqueous base, which is also a poison for the acidic ion exchange resin catalyst.

It is therefore an object of the present invention to provide an acid-catalyzed bisphenol preparation process employing an acidic resin catalyzed isomerization process with improved product purity and yield.

SUMMARY OF THE INVENTION

According to the invention, a process for the production of a bisphenol is provided, the process comprising the steps of:
(a) reacting a carbonyl compound with a stoichiometric excess of a phenolic compound in the presence of an effective amount of an acidic catalyst: to produce a reaction product mixture comprising a bisphenol and a bisphenol by-product;
(b) passing at least a portion of said reaction product mixture to a crystallization zone maintained under conditions effective to produce a crystalline bisphenol and a mother liquor comprising the bisphenol by-product;
(c) contacting, in an isomerization zone, at least a portion of said mother liquor with an acidic ion exchange resin isomerization catalyst under conditions effective to convert at least a portion of said bisphenol by-product to said bisphenol, to produce a isomerization reaction product mixture comprising the bisphenol;
(d) contacting the isomerization reaction product mixture with a guard bed selected from the group consisting of alumina, silica, titanium oxide, zirconium oxide, tin oxide, carbon, and silicon carbide; and
(e) recovering the bisphenol from the thus-treated isomerization reaction product mixture.

DETAILED DESCRIPTION OF THE INVENTION

Figure 1:
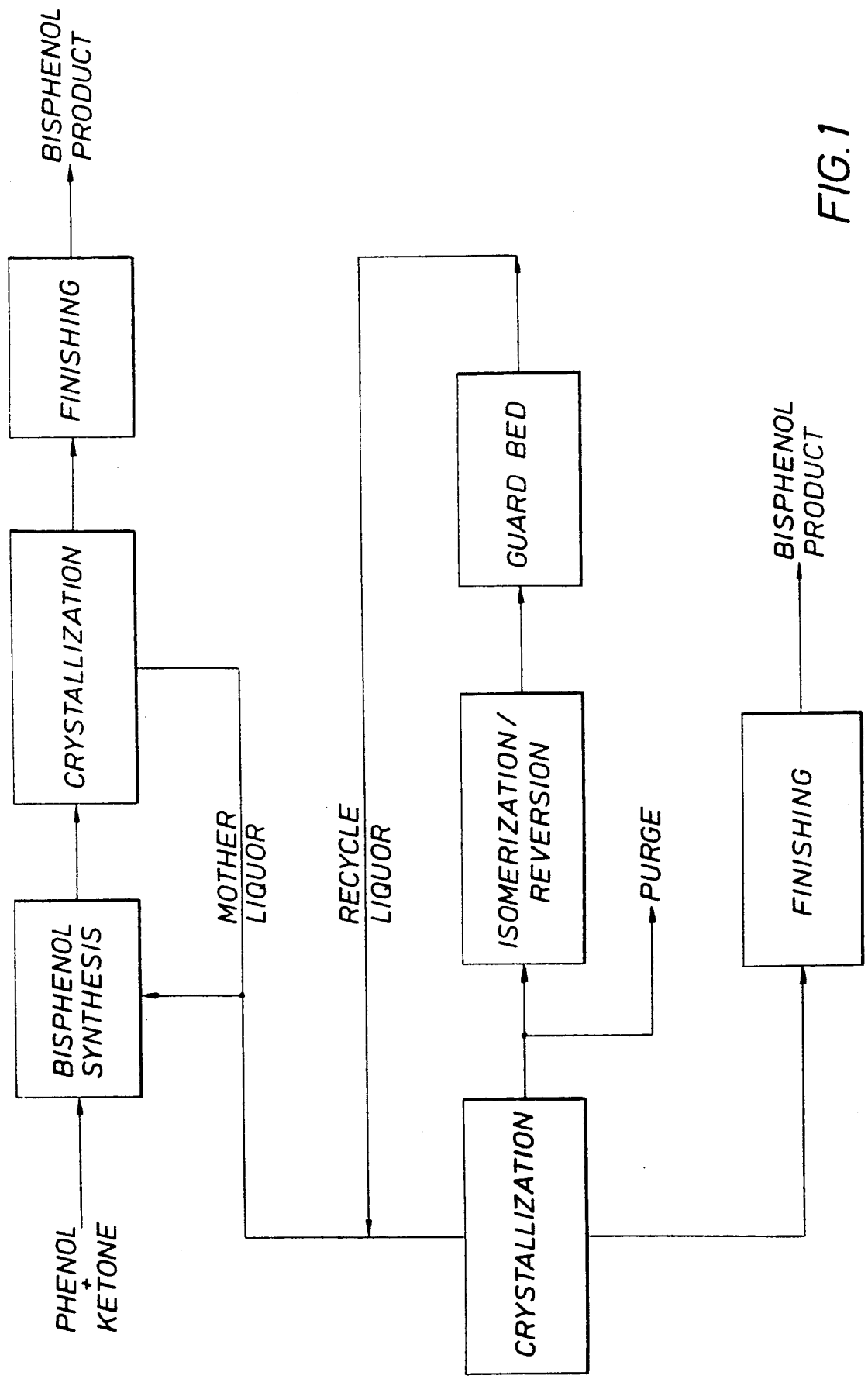
FIG. 1 is a schematic flow diagram illustrating an embodiment of the invention process.

The phenolic compound employed as the starting material in the production of bisphenols can be any compound containing hydroxyl group linked to a carbon of an aromatic group. Suitable phenolic compounds include, for example, phenols and substituted phenols, such as: phenol, cresols, xylenols, chlorophenols, thymol, carvacrol, cumenol, 2-methyl-6ethylphenol, 2,4-dimethyl-3-ethylphenol, 4-ethylphenol, 2-ethyl-4-methylphenol, 2,3,6-trimethylphenol, 2-methyl-4-tertiary-butylphenol, Z,4-ditertiary-butyl-phenol, 4-methyl-Z-tertiary-butylphenol, 2-tertiary-butyl-4methylphenol, 2,3,5,6-tetramethylphenols, 2,6-dimethylphenol, 2,6-ditertiary-butylphenol, 3,5-dimethylphenol, 3,5-diethylphenol, 2-methyl-3,5-diethylphenol, o-phenylphenol, p-phenylphenol, tetraphenolethane, the naphthols, phenanthrol, their homologues and analogues. Suitable phenolic compounds include those containing one or more phenolic group in each nucleus as well as polynuclear compounds.

The carbonyl compound employed as the starting material can be any compound of the following formula:

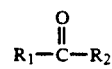

wherein $R_1$ represents a member of the group consisting of any aliphatic, cycloaliphatic, aromatic and heterocyclic radicals, and $R_2$ represents a member of the group consisting of hydrogen, aliphatic, cycloaliphatic, aromatic and heterocyclic radicals. Suitable carbonyl compounds include ketones and aldehydes. Examples of suitable ketones include, for example, acetone, 1,3-dichloroacetone, dimethyl ketone, methyl ethyl ketone, diethyl ketone, dibutyl ketone, methyl isobutyl ketone, cyclohexanone, fluorenone, propionylphenone, methyl amyl ketone, mesityl oxide, cyclopentanone, acetophenone, and examples of suitable aldehydes include formaldehyde, acetaldehyde, propionaldehyde, butyraldehyde and benzaldehyde.

The specific phenolic compound and carbonyl compound employed as starting material will depend upon the specific bisphenol compound desired and may be governed to some extent by specific operating conditions employed. The invention process is particularly suitable for production of bisphenol-A, for which the carbonyl compound is acetone and the phenolic compound is phenol. Typically, excess phenol is used for the condensation reaction. The preferred ratio of phenol to carbonyl compound is within the range of about 20:1 to 2:1, generally about 12:1 to 2:1.

For the condensation reaction of a phenolic compound and a carbonyl compound, any suitable acid catalyst can be used. Suitable acid catalysts include acidic ion exchange resin catalysts and soluble acid catalysts. Soluble acid catalysts can be for example, hydrogen chloride, sulfuric acid, hydrochloric acid, phosphoric acid, hydrobromic acid, nitric acid, dimethylsulfate, sulfur dioxide, p-toluene sulfonic acid, boron trifluoride, boron trifluoride complexes and other acid-acting compounds comprising compounds which are hydrolyzed by water to form acids such as aluminum chloride, sulfonyl chloride and phosgene. Anhydrous hydrogen chloride is preferred. Acidic ion exchange resins usable in the condensation reaction include essentially all known acidic ion exchange resins. Sulfonated resins are generally preferred. In particular, a sulfonated aromatic organic polymer as the ion exchange resin catalyst is quite suitable.

Various acidic ion exchange resins are disclosed, for example, in U.S. Pat. Nos. 2,597,438, 2,642,417, 3,172,916, 3,394,089, 3,634,341, 4,045,379, 4,396,728 and 4,455,409. Some examples of suitable commercially available sulfonated resins are: M-31 and G-26 manufactured by Dow Chemical Company; A-15, A-31, A-32, XE-383 and XE-386 manufactured by Rohm and Haas; and SC-102 and SC-104 manufactured by Bayer-Lewatit.

For the isomerzation/reversion reaction the same acidic ion exchange resins as listed above are suitable. In particular, a sulfonated aromatic organic polymer is preferred.

The condensation and the isomerization step can optionally be executed in the presence of an added promoter for the acid-catalyzed reaction. Any known promoter for the acid catalyzed condensation of a phenolic compound and a carbonyl compound or acid-catalyzed isomerzation/reversion of bisphenol by-products is suitable. Suitable promoters include mercaptan groups which are either free or bound to a resin. Alkyl mercaptans and bis-mercapto ethanolamine are examples of suitable promoters for the invention process.

The precise amount of acidic ion exchange resin to be used in reversion/isomerization reactions depends upon the specific resin, feed temperature, and conditions employed. Feed rates may typically vary from about 20 pounds feed per pound catalyst per hour, to 0.1 pounds of feed per pound of catalyst per hour. The isomerization/reversion reaction is usually conducted in the presence of small amounts of water, ranging from about 1.5% to nearly anhydrous conditions. Higher water concentrations may be used, but generally at the expense of catalyst efficiency. Temperatures for the isomerization/reversion reaction step typically range from about 50 to about 130° C.

According to the invention, a high purity bisphenol such as the bisphenol of acetone (bisphenol-A) can be produced from revertible byproducts of bisphenol synthesis by contacting an isomerization reaction effluent mixture with a bed of solid particles. Revertible by-products are produced along with the desired p,p'-bisphenol during the synthesis by contacting a carbonyl compound with a stoichiometric excess of a phenolic compound in the presence of an acid catalyst. Isomerization product mixture is the effluent of an isomerization/reversion zone wherein the by-products are isomerized/reverted in the presence of an effective amount of an acidic ion exchange resin catalyst.

In order to obtain bisphenols with higher purities according to the invention process, the effluent of the isomerization reaction zone is contacted with a solid particle bed under conditions effective to remove any of the acidic fines from the effluent. The packed bed of solids which can be employed as a guard bed include alumina, zirconium oxide, titanium oxide, tin oxide and silica. In addition, carbon, activated carbon, or silicon carbide may be employed. Preferably, the solid particles will be nonspherical, in order to provide maximal filtration efficiency. The guard bed itself should not contain an appreciable amount of very small particles ("dust"), or the small particles should be removed prior to streaming of the bed via an appropriate wash. Alumina, titanium oxide, zirconium oxide and carbon are preferred, and alumina and carbon are most preferred.

Any size of solid particles may be employed. Typically, the solid particles will range from about 200 mesh to about 4 mesh. Optimal size of the solid particles will be determined by the pressure drop required to force liquid flow through the bed. As particle size is increased under otherwise fixed operating conditions, pressure drop will decrease, at the expense of filtration efficiency. Generally, solid particles between 12 and 40 mesh will be optimal for filtration of a liquid stream. Linear velocity, defined as the volumetric rate of flow divided by the empty vessel cross sectional area, may typically range from about 1 to about 300 ft/hr, and is preferably from about 5 to about 100 ft/hr.

The guard bed can be located at any position downstream from the isomerization zone and upstream from the final step of product purification. Preferably, the guard bed is located downstream from the isomerization zone and upstream from any section where heat is employed to remove excess carbonyl reactant (from the bisphenol synthesis), phenol, water, and/or free mercaptan promoter as overhead fractions.

Effluents from the guard bed can be passed to a crystallization step before routing of purified crystals to a final finishing section. Alternatively, effluent from the guard bed may be recycled back to the bisphenol synthesis step.

The solid bed may be operated in an upflow or downflow configuration. If operated in an upflow mode, it is desirable to select particle size and linear velocity to minimize fluidization or expansion of the packed bed from its static height.

In a preferred embodiment of the present invention, the guard bed is operated in a downflow mode. Flow through the bed is then periodically reversed to backflush filtered particulates out of the system and restore filter capacity of the bed. During backflush, the bed is typically fluidized or expanded by about 10% to about 100% of the static bed height.

A preferred embodiment of the invention entails use of an inorganic oxide adsorbent exhibiting an isoelectric point (pI) greater than the PH of the isomerization/reversion reaction mixture. With such an adsorbent, soluble acid abstraction via adsorption or ion exchange may be combined with filtration of solid acid resin fines. Alternately, an activated carbon may be employed to combine adsorption and filtration functions.

The temperature of the guard bed may be any temperature sufficiently high to prevent freezing of the liquid effluent stream from the isomerization zone and sufficiently low so as not to cause excessive degradation of desired p,p'-bisphenol isomer or the solid particle bed itself. An increase in temperature will generally reduce the solution viscosity and hence lower the pressure drop through the guard bed. The solid particle or adsorbent bed may exhibit some catalytic properties in degrading the desired product, however, and hence upper temperature limits will depend upon the nature of the solid particles employed For catalyst fines removal via a silica, alumina, or carbon bed during synthesis of bisphenol-A, temperatures between 50 and 130° C. will typically be employed.

For convenience, the invention process will be specifically described in terms of its most preferred embodiment, in which acetone and an excess of phenol are contacted in a reaction zone in the presence of a sulfonated cationic exchange resin catalyst and free mercaptan to produce bisphenol-A (BPA). The reaction is carried out in one or a series of reactors operated at temperatures within the range of about 60 to about 95° C. The reaction effluent includes BPA, acetone, water, mercaptan, phenol and various phenolic by-products of the reaction. After removal of a portion of the excess phenol by flashing, the effluent is optionally passed through a fixed bed adsorbent such as alumina or carbon for removal of any leached acid.

Alternatively, acetone and an excess of phenol can be contacted in a reaction zone in the presence of HCl catalyst and free mercaptan to produce BPA. The reaction is carried out in one or a series of reactors operated at temperatures within the range of about 20 to about 85° C. HCl and a portion of excess phenol are removed by flashing before recovery of the desired BPA.

Subsequently, a major portion of the bisphenol from the reaction product mixture is removed from the effluent. Suitable means for recovering bisphenols include one or more of such steps as distillation, solvent extraction, stratification, extractive distillation, adsorption, crystallization, filtration, centrifugation and thermal liberation. Typically, the BPA is isolated by passing the reaction product stream containing BPA to a crystallization zone, where the stream is cooled to crystallize a BPA-phenol adduct or treated with water to crystallize the BPA. Slurries of crystallized BPA or crystalline adducts of BPA are separated from the remaining solution by filtration or by centrifugation and at least a portion of the remaining filtrate or "mother liquor" is passed to the isomerization zone via an optional phenol flashing step.

In the isomerization zone, the mother liquor is combined optionally with a recycle liquor from the effluent of the isomerization zone treated according to the invention process, and contacted with a sulfonated cationic exchange resin catalyst !or conversion of revertible by-products to the desired p,p'-BPA. Alternatively, the combined liquor can be passed through an additional crystallization zone for further removal of the desired BPA and subsequently passed to the isomerization zone. The reaction is carried out in one or a series of isomerization reactors operated at temperatures within the range of about 50 to about 130° C. The isomerization reaction effluent includes BPA, acetone, water, mercaptan, phenol, and non-revertible phenolic by-products, and may include acid and fines leached from the catalyst. The isomerization reaction mixture is then contacted with a guard bed as described above at temperatures within the range of about 50 to about 130° C. to filter acidic fines and to remove acids.

Subsequently, the desired BPA can be purified and removed from the treated effluent by the various methods described above. BPA from the isomerization zone can be combined with the effluent of the BPA synthesis and recovered, or recovered independently for subsequent use. Optionally, when BPA is separated from the treated effluent independently by filtration or centrifugation, the remaining filtrate or "recycle liquor" can be recycled to the isomerization zone.

Alternatively, the guard bed treated isomerization reaction effluent can be combined with the mother liquor from the condensation reaction prior to recovering the desired BPA by crystallization as described in FIG. 1. In such a process, the treated effluent can thus be recycled prior to the crystallization step to the additional crystallization zone described above as shown in FIG. 1.

In a finishing zone, BPA isolated as a crystalline adduct is converted to BPA by thermally stripping phenol from the adduct, and recrystallizing. More than one such step can be employed in the finishing zone to purify BPA.

The BPA product of the invention process has improved purity and yield, as particles are removed and acid-catalyzed cracking of the product is reduced. The invention process provides a conveniently recyclable system without significant risk of contamination of the acidic ion exchange resin catalyst. This is advantageous particularly in a system in which the recycle liquor is returned to the isomerization reactor.

EXAMPLE 1

This example demonstrates that an alumina bed will effectively 5 filter catalyst fines from a BPA effluent stream. A sulfonic acid resin was stained with methylene blue and crushed. The crushed resin was added to the top of an 6-inch tall bed of 14×28-mesh F1 alumina substrate, housed in a 1-inch diameter glass column. Deionized water was flowed downward over the bed at a linear velocity of 0.6 ft/minute. The dark blue resin was readily discerned from the white alumina bed. After 72 hours of flow, virtually all of the resin remained on top of the alumina bed. Maximum penetration distance into the bed was one inch.

EXAMPLE 2

For comparison, this example demonstrates migration of fines j through a resin bed. Five grams of a sulfonic acid resin were stained with methylene blue and crushed. Crushed fines were added to the bottom of a 1-inch diameter glass column containing a 12.5-inch tall bed of unstained, uncrushed resin. Water was passed upflow through the bed at a slow rate which gave less than 10% expansion of the bed. The stained, crushed resin was observed to quickly migrate to the top of the bed and again form a sharp blue band. The time for this migration corresponded to that estimated for liquid flow from knowledge of the interstitial velocity of liquid through the bed. Rapid "classification" of resin fines in this manner indicates negligible filtration of the fines by the resin bed. Hence, resin fines present in the bed will elute from the bed under flowing conditions. Because low bed expansion was employed in the above test, elution of fines during downflow operation of the bed is also expected.

EXAMPLE 3

This example demonstrates the effective removal of the acidity by alumina. Between 0.01 and 0.05 grams of dried crushed sulfonic acid resin (5 milliequivalents per gram acid capacity) were placed in jars containing 200 grams of deionized water. The solutions were then filtered via 47-mm filter paper, and the filter was treated ultrasonically in 40 cc of deionized water in a titration flask and washed with an additional 20 cc of water. The resulting fines slurry was titrated with 0.01N KOH delivered at a nominal rate of 25 microliters/minute via a microprocessor controlled titroprocessor. After correction for blank runs with no catalyst fines, results indicated that between 80 and 95% of the original acidity charged to the standard jars was titrated. This calibration thus established the ability to titrate any desired concentration of acidic resin fines via adjustment of total volume of filtered solution.

Five grams of crushed resin were added to 200 cc of deionized water. The slurry was mixed and allowed to settle for 15 minutes. Suspended fines were then decanted into a second bottle, which now contained only suspendible fines. An aliquot of the second slurry was titrated directly, for comparison with other aliquots which were filtered as described above, before titration. The filtration method yielded 65% of the acidity indicated in the direct titration, which establishes an ability to titrate very small, suspendible resin fragments via the filtration/titration method described above.

A slug of the suspendible fines slurry was added to the top of a 12.8 inch bed of 14×28-mesh F1 alumina. Deionized water was flowed downward through the bed at a rate of 10 ft/hr. Discrete samples of effluent were collected, filtered and titrated for acidity using the method described above. Maximum acidity in the effluent attributed to catalyst fines was less than 2% of the fines acidity in the initial slurry. Total acidic fines elution was less than 5% of the total fines acidity injected to the column.

EXAMPLE 4

This example demonstrates that the purity of a BPA product is improved by treatment of a BPA-containing effluent according to the invention process. Shortly after streaming of an isomerization reactor containing a sulfonic acid resin catalyst, the phenol impurity concentration in the BPA product increased from 100–300 ppm to greater than 3000 ppm. Soluble acid concentrations in the reactor effluent were not significant. Phenol impurities in 8PA product decreased to baseline values after bypassing of the isomerization reactor. Phenol is known to be a principal impurity formed via acid-catalyzed cracking of bisphenols.

The isomerization unit was restreamed with a downstream guard bed of 14×28-mesh F1 alumina, operated in a downflow mode at a linear velocity of approximately 8–12 ft/hr. Samples of the isomerizer bed effluent (analyzed via the filtration/titration procedure described above) revealed up to 5 parts per million of acidic resin fines after restreaming, which could catalyze formation of more than 1000 ppm phenol impurity during thermal finishing. Similarly, soluble sulfonic acid leached from the resin during the interim had risen to 450 ppmw, which would also cause significant product degradation during subsequent product finishing. After restreaming with the guard bed, phenol impurities in the BPA product remained at their baseline levels (100–300 ppm) as a result of acid resin fines filtration and soluble acid adsorption provided by the packed bed of alumina.

We claim:

1. A process for the production of a bisphenol comprising the steps of:
  (a) reacting a carbonyl compound selected from the group consisting of ketones and aldehydes having the general formula:

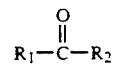

wherein $R_1$ is selected from the group consisting of aliphatic, cycloaliphatic and aromatic radicals, and $R_2$ is selected from the group consisting of aliphatic, cycloaliphatic, aromatic radicals and hydrogen, with a stoichiometric excess of a phenolic compound in the presence of an effective amount of an acid catalyst to produce a reaction product mixture comprising a bisphenol and a bisphenol by-product;
  (b) passing at least a portion of said reaction product mixture to a crystallization zone maintained under conditions effective to produce a crystalline bisphenol and a mother liquor comprising the bisphenol by-product;
  (c) contacting, in an isomerization zone, at least a portion of said mother liquor with an effective amount of an acidic ion exchange resin isomerization catalyst to convert at least a portion of said bisphenol by-product to said bisphenol, to produce an isomerization reaction product mixture comprising the bisphenol;
  (d) contacting the isomerization reaction product mixture with a guard bed selected from the group consisting of alumina, silica, titanium oxide, zirconium oxide, tin oxide, carbon, and silicon carbide; and
  (e) recovering the bisphenol from the thus-treated isomerization reaction product mixture.

2. The process of claim 1 wherein the carbonyl compound is selected from the group consisting of acetone, 1,3-dichloroacetone, dimethyl ketone, methyl ethyl ketone, diethyl ketone, dibutyl ketone, methyl isobutyl ketone, cyclohexanone, fluorenone, propionylphenone, methyl amyl ketone, mesityl oxide, cyclopentanone, acetophenone, formaldehyde, acetaldehyde, propionaldehyde, butyraldehyde and benzaldehyde.

3. The process of claim 1 wherein the carbonyl compound is a ketone.

4. The process of claim 3 wherein the carbonyl compound is acetone.

5. The process of claim 1 wherein the guard bed is selected from the group consisting of alumina, zirconium oxide, titanium oxide, tin oxide and carbon.

6. The process of claim 5 wherein the guard bed is selected from the group consisting of alumina, zirconium oxide, titanium oxide and tin oxide.

7. The process of claim 5 wherein the guard bed is selected from the group consisting of alumina and carbon.

8. The process of claim 7 wherein the guard bed is alumina.

9. The process of claim 1 wherein the isomerization reaction product mixture is contacted with the guard bed within the range of rom about 50° C. to about 130° C.

10. The process of claim 1 in which the crystalline bisphenol of step (b) comprises a bisphenol/phenol adduct.

11. The process of claim 1 in which step (b) further comprises combining a portion of said mother liquor with the treated isomerization reaction product mixture from step (d) to produce a combined product mixture comprising the bisphenol product, and then passing said combined product mixture to a second crystallization zone maintained under conditions effective to produce a crystalline bisphenol and the mother liquor comprising the bisphenol by-product.

12. The process of claim 1 in which step (e) comprises passing the thus-treated isomerization reaction product mixture to a crystallization zone to produce a bisphenol/phenol adduct and a recycle liquor.

13. The process of claim 12 in which the bisphenol/phenol adduct is combined with a bisphenol/phenol adduct from step (b) and recovering the bisphenol from the combined bisphenol/phenol adduct.

14. The process of claim 12 which further comprises passing at least a portion of the recycle liquor to the isomerization zone.

15. The process of claim 12 in which the bisphenol is recovered from the bisphenol/phenol adduct independently from a bisphenol/phenol adduct from step (b).

16. The process of claim 11 in which step (e) comprises passing at least a portion of the thus-treated isomerization reaction product mixture back to the second crystallization zone.

17. A process for the production of a bisphenol comprising the steps of:
(a) reacting a carbonyl compound selected from the group consisting of ketones and aldehydes having the general formula:

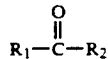

wherein $R_1$ is selected from the group consisting of aliphatic, cycloaliphatic and aromatic radicals, and $R_2$ is selected from the group consisting of aliphatic, cycloaliphatic, aromatic radicals and hydrogen, with a stoichiometric excess of a phenolic compound in the presence of an effective amount of an acid catalyst to produce a reaction product mixture comprising a bisphenol and a bisphenol by-product;
(b) passing at least a portion of said reaction product mixture to a first crystallization zone maintained under conditions effective to produce a crystalline bisphenol and a mother liquor comprising the bisphenol by-product;
(c) passing at least a portion of said mother liquor to a second crystallization zone maintained under conditions effective to produce a crystalline bisphenol and a second mother liquor comprising the bisphenol by-product;
(d) contacting, in an isomerization zone, at least a portion of said second mother liquor with an effective amount of an acidic ion exchange resin isomerization catalyst to convert at least a portion of said bisphenol by-product to said bisphenol, to produce an isomerization reaction product mixture comprising the bisphenol;
(e) contacting the isomerization reaction product mixture with a guard bed selected from the group consisting of alumina, silica, titanium oxide, zirconium oxide, tin oxide, carbon, and silicon carbide; and
(f) passing at least a portion of the thus-treated isomerization reaction product mixture back tot he second crystallization zone.

18. The process of claim 17 wherein the carbonyl compound is selected from the group consisting of acetone, 1,3-dichloroacetone, dimethyl ketone, methyl ethyl ketone, diethyl ketone, dibutyl ketone, methyl isobutyl ketone, cyclohexanone, fluorenone, propionylphenone, methyl amyl ketone, mesityl oxide, cyclopentanone, acetophenone, formaldehyde, acetaldehyde, propionaldehyde, butyraldehyde, butraldehyde and benzaldehyde.

19. The process of claim 17 wherein the carbonyl compound is a ketone.

20. The process of claim 17 wherein the carbonyl compound is acetone.

21. The process of claim 17 wherein the guard bed is selected from the group consisting of alumina, zirconium oxide, titanium oxide, tin oxide and carbon.

22. The process of claim 21 wherein the guard bed is selected from the group consisting of alumina and carbon.

23. The process of claim 22 wherein the guard bed is alumina.

24. The process of claim 17 wherein the isomerization reaction product mixture is contacted with the guard bed within the range of from about 50° C. to about 130° C.

25. The process of claim 17 in which the crystalline bisphenol of step (b) comprises a bisphenol/phenol adduct.

26. The process of claim 17 in which step (c) comprises subjecting at least a portion of the mother liquor and a portion of the treated isomerization reaction product mixture from step (f) to conditions effective for crystallization of a bisphenol/phenol adduct and recovering the bisphenol from the bisphenol/phenol adduct.

* * * * *